United States Patent [19]

Presser et al.

[11] Patent Number: 4,713,002
[45] Date of Patent: Dec. 15, 1987

[54] DENTAL MIRROR

[75] Inventors: Dwight W. Presser, West Bloomfield Township, Oakland County, Mich.; Joseph J. Berke, 3333 E. Jefferson St., Detroit, Mich. 48207

[73] Assignee: Joseph J. Berke, Bloomfield Hills, Mich.

[21] Appl. No.: 785,922

[22] Filed: Oct. 9, 1985

[51] Int. Cl.$^4$ .......................... A61C 1/00; A61C 3/00
[52] U.S. Cl. ..................................................... 433/30
[58] Field of Search ..................................... 433/29, 30

[56] References Cited

U.S. PATENT DOCUMENTS

| 516,092 | 3/1894 | Hills | 433/30 |
| 3,512,259 | 5/1970 | Gordon et al. | 433/30 |
| 4,294,356 | 10/1981 | Abramowitz | 433/30 |

Primary Examiner—Robert Peshock
Attorney, Agent, or Firm—Cullen, Sloman, Cantor, Grauer, Scott & Rutherford

[57] ABSTRACT

An improved dental mirror or instrument of the type including an elongated handle and a disc-like mirror mounted in a frame at one end of the handle. A concave clear plastic shell is sealed relative to the mirror surface to substantially reduce, if not completely eliminate, condensation. The concave exterior surface, which is dome-like in configuration, may be comfortably and conveniently wiped on the inside cheek of the patient to assist in maintaining the surface clear and clean, and to assist in removal of debris from the mouth of the patient.

14 Claims, 5 Drawing Figures

DENTAL MIRROR

BACKGROUND OF THE INVENTION

This invention relates to dental mirrors and, more particularly, to an improved dental mirror or other medical-surgical instrument which substantially reduces clouding or fogging by moisture condensation, and which additionally aids the dentist in the removal of debris particles from the mouth of the patient.

Dental mirrors are, of course, well known. Equally well known, of course, is the fact that during use of the dental mirror a substantial problem arises in that condensation on the mirror causes a clouding or fogging of the mirror and thus impairs the field of vision for the dentist.

Numerous techniques have been suggested, in the past, for reducing condensation on a dental mirror. For example, U.S. Pat. No. 2,625,858 to Dreher suggests a dental mirror handle with high thermal conductivity such that heat from the dentist's hand is conducted to the mirror thereby warming the mirror until the mirror temperature is quite close to the temperature of the patient's breath. A second approach, as reflected by numerous patents such as U.S. Pat. No. 3,014,279 to Fosdal, suggests an airstream to be directed onto the face of the mirror. The Fosdal patent also includes a reservoir of detergent in the handle to aid in cleaning the mirror. The use of a wetting agent to keep a mirror clear is suggested, for example, in U.S. Pat. No. 3,151,395 to Moniot.

Prior to the present invention, however, none of the aforementioned techniques have achieved any degree of commercial success or commercial viability. Accordingly, prior to the present invention, there has been no satisfactory approach to the problem of condensation impairing the field of vision for the dentist.

SUMMARY OF THE INVENTION

The present invention overcomes the aforementioned disadvantages by providing a new and improved approach to the problem of condensation on the face of a dental mirror. A dental mirror, of course, typically includes an elongated handle or shaft having an oval or circular mirror secured to the handle. The mirror may be set at an obtuse angle to the shaft.

The present invention contemplates a protective covering over the mirror surface with the protective covering which may be in air tight contact with, or hermetically sealed to, the mirror such that air is precluded from entering any space between the mirror and the protective covering. The preferred protective covering or coating is made of a clear plastic and is preferably domed or convex. The preferred protective coating may be sealed to the mirror by a snap fit or by a molding process, or threaded onto the mirror frame. A gas, liquid (such as mineral oil), semi-solid or solid plastic may be interposed between the coating and the mirror to enhance the optical quality of the mirror system.

BRIEF DESCRIPTION OF THE DRAWINGS

The various benefits of the present invention, together with numerous other objects, advantages and benefits which may be attained by its use, will become more apparent upon reading the following detailed description of the invention taken in conjunction with the drawings.

In the drawings, wherein like reference numerals identify corrresponding components.

DETAILED DESCRIPTION OF THE INVENTION

Figure 1:
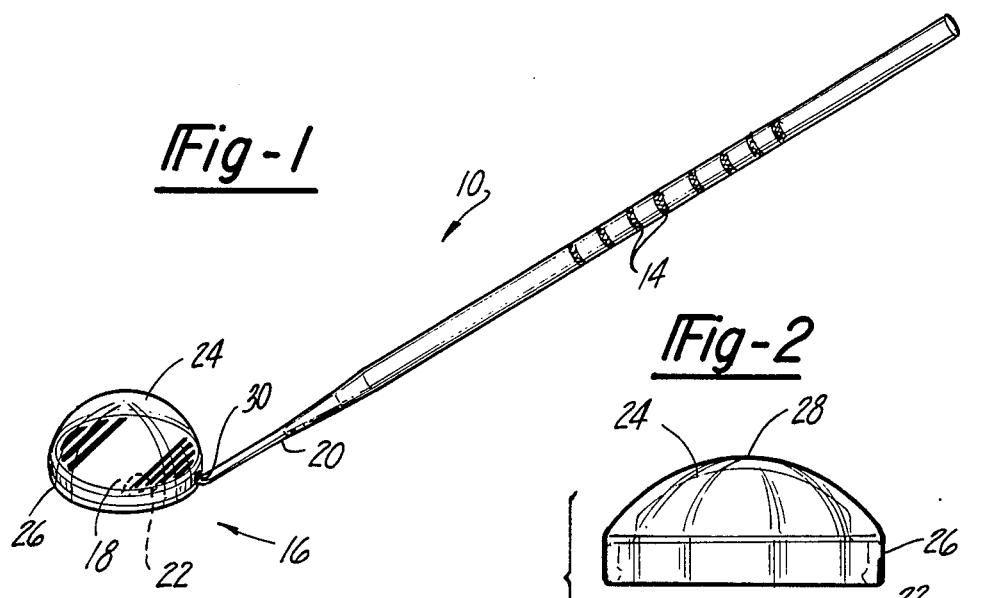
FIG. 1 is a perspective illustration of a dental mirror according the principles of the present invention.

With reference to the drawings, the present invention will now be explained. A dental mirror 10 is illustrated generally in FIG. 1 including an elongated handle 12 which may have a knurled portion 14. The knurled portion, of course, is provided to enhance holding, or gripping, and control of the dental mirror. The dental mirror 10 includes, at one end of the handle, a mirror portion 16 which typically includes a frame 18 secured to a stem 20. The stem 20 is provided at an obtuse angle to the plane of the frame such that upon inserting the dental mirror into the mouth of the patient, the obtuse angle provides for a better field of vision. The stem may have a male threaded portion at the end opposite the mirror frame which threaded portion may fit into a threaded socket in the handle. This aspect of a dental mirror is, of course, conventional.

Mounted within the frame 18 is a disc-like mirror 22 which may be either front-surfaced or back-surfaced. Heretofore, the mirror as described would be conventional.

Figure 2:
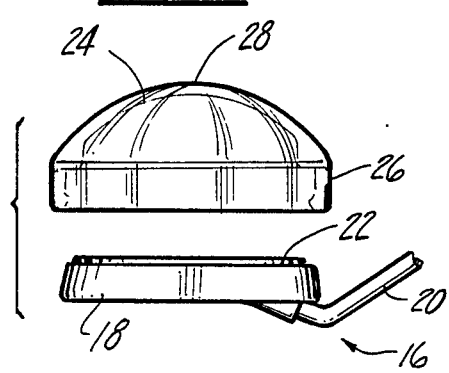
FIG. 2 is a partial, exploded front elevation view of a dental mirror including the protective covering or coating of the present invention.
Figure 3:
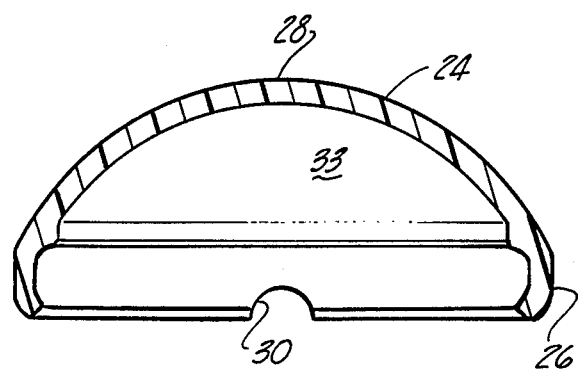
FIG. 3 is an enlarged elevation view, partly in section, of the protective covering or coating of the present invention.

According to the principles of the present invention, the reduction or substantial elimination of moisture condensation on the mirror is accomplished through the provision of a protective covering or coating 24. In the embodiment illustrated in FIGS. 1, 2 and 3, the protective covering or coating is formed as a convex shell having a lip or rim 26 and a dome 28. The protective covering may be generally thought of as having the configuration of a portion of the surface of a sphere or ovoid formed by slicing through the sphere (or ovoid) parallel to a diameter and intermediate the diameter and polar region or end of the sphere (or ovoid). The dome portion may be slightly flattened if desired as will be explained further.

In one form of the invention, the protective covering or coating may include a notch 30 within the lip or rim 26 to fit over the stem 20 of the mirror portion of the dental mirror.

Figure 5:
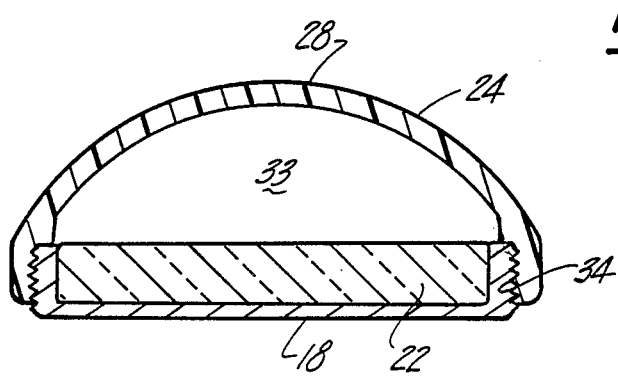
FIG. 5 is an enlarged elevation view, partly in section, of the protective covering or coating threaded onto the mirror frame.

It is important to provide an air tight relationship between the mirror surface and the interior of the protective covering. This may be accomplished in one of several ways. First, the protective covering may be force-fit or snapped into place with the lip 26 engaging the mirror frame 18. Alternatively, there may be a bezel-type fitting between the protective covering and the frame much that the way a watch crystal is secured to a waterproof wristwatch. FIG. 5 illustrates yet another technique as will be explained later.

There are various important considerations in the selection of a proper material for the protective covering 24. The material is preferably transparent and will preserve the optical properties when an image is reflected back from the mirror through the coating. Hence maintaining if not improving color and clarity are important attributes of the protective coating. The protective covering or coating may include a thin layer of anti-reflective material which is commonly used in the optical fields such as aluminum oxide or magnesium oxide and this may be provided on both sides of the dome 28 of the protective covering itself.

Figure 4:
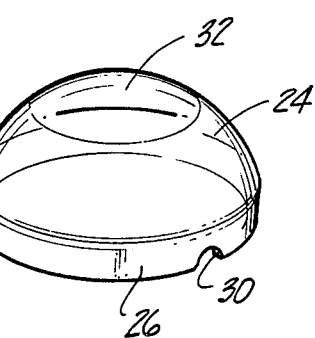
FIG. 4 is a perspective illustration of a second version of the protective covering or coating.

Preferably, the protective coating may be made of a styrene which is easy to mold and has excellent optical properties among the plastics; polycarbonates may be used in that they are stronger but somewhat more difficult to mold and work with. Nitrogen or other gas may be positioned between the mirror facing and the bubble and sealed therein to further reduce mirror fogging. As illustrated in FIG. 4, the dome 28 may be provided with a magnifying section 32 to provide an enhanced or enlarged visual image. If there is a space or region 33 between the covering and the mirror, this space may be evacuated or filled with a gas, liquid (mineral oil), solid or semi-solid to enhance the optical properties of the mirror.

FIG. 5 illustrates another form of the invention where the coating is threaded, as at 34, onto the frame to provide the air tight relationship.

In addition to the use of a styrene material, it has been found that a presently preferred material is polymethylpentene.

It should also be understood and appreciated that it is within the spirit and scope of the present invention to provide a protective coating in the nature of a thin film on the mirror and even by dipping the mirror in a plastic to form a coating. Of course, with such a coating there may not be any space 33 between the coating and the mirror.

The dome is important for several reasons. First, there may always be some condensation on the mirror and to the extent that such condensation does, in fact, occur on the protective covering, the dome configuration provides a convenient and comfortable surface to be wiped on the inside of the mouth, more particularly the check of the patient to thus remove any condensation. The configuration of dental mirrors at present precludes such a technique because the flat mirror surface cannot be conveniently and comfortably wiped on the interior cheek of the patient.

Secondly, when dentists are working on teeth of their patients, whether cleaning, drilling or virtually any other procedure, the combination of saliva from the patient, particles from drilling, water utilized by the dentist to irrigate the area where the dentist is working and/or pressurized air utilized by the dentist to clear the area where the dentist is working all contribute to the movement of particles within the mouth of the patient which particles will, of necessity, come in contact with the face of a dental mirror. The dental mirror of the present invention, by providing a dome configuration (spherical, ovoid, etc.), provides an improvement in that the dome can always be wiped clear more easily, on the interior cheek of the patient, even if there is no condensation problem.

The principals of the present invention may be used in other instruments employed in medical-surgical procedures, whether on humans or animals, where a mirror or reflective surface is employed.

The foregoing is a complete description of a preferred embodiment of the present invention. Various changes and modifications may be made without departing from the spirit and scope of the present invention. The invention, therefore, should be limited only by the following claims.

What is claimed is:

1. In an instrument of the type including an elongated handle and a disc-like mirror mounted at one end of the handle, said mirror having a mirror face, the improvement comprising:
   a protective shield over the disc-like mirror, the protective shield sealed relative to said mirror face to prevent fluids from entering therebetween; and
   the protective shield is formed as a portion of a sphere.

2. In an instrument of the type including an elongated handle and a disc-like mirror mounted at one end of the handle, said mirror having a mirror face, the improvement comprising:
   a protective shield over the disc-like mirror, the protective shield sealed relative to said mirror face to prevent fluids from entering therebetween; and
   the protective shield is formed as a portion of an ovoid.

3. In an instrument of the type including an elongated handle and a disc-like mirror mounted at one end of the handle, said mirror having a mirror face, the improvement comprising:
   a protective shield over the disc-like mirror, the protective shield sealed relative to said mirror face to prevent fluids from entering therebetween; and
   the protective shield is snap fit into the dental mirror.

4. In an instrument of the type including an elongated handle and a disc-like mirror mounted at one end of the handle, said mirror having a mirror face, the improvement comprising:
   a protective shield over the disc-like mirror, the protective shield sealed relative to said mirror face to prevent fluids from entering therebetween; and
   the protective shield includes a magnifying portion.

5. In an instrument of the type including an elongated handle and a disc-like mirror at one end of the handle, said mirror having a mirror face, the improvement comprising:
   a protective shield over the disc-like mirror, the protective shield sealed relative to said mirror face to prevent fluids from entering therebetween; and
   an anti-reflective layer is provided on at least one side of the protective shield.

6. The instrument as defined in claims 1, 2, 3, 4 or 5 wherein the protective shield is generally concave and includes a lip portion sealed to the dental mirror face and a raised dome spaced apart from the dental mirror face.

7. The instrument as defined in claims 1, 2, 4 or 5 wherein the protective shield is snap fit into the dental mirror.

8. The instrument as defined in claims 1, 2, 4 or 5 wherein the protective shield is threaded onto the dental mirror.

9. The instrument as defined in claims 1 or 5 wherein the protective shield includes a magnifying portion.

10. The instrument as defined in claims 1, 2, 3, 4 or 5 wherein nitrogen gas is positioned between the protective shield and the mirror.

11. The instrument as defined in claims 1, 2, 3, 4 or 5 wherein means are provided to enhance the optical quality of the image.

12. The instrument as defined in claim 1 wherein the protective shield is formed of a styrene.

13. The instrument as defined in claim 1 wherein the protective shield is formed of a polycarbonate.

14. The instrument as defined in claim 1 wherein the protective shield is formed of polymethylpentene.

* * * * *